United States Patent [19]
Dane et al.

[11] Patent Number: 5,843,387
[45] Date of Patent: *Dec. 1, 1998

[54] STERILIZATION AND STORAGE CONTAINER TRAY

[75] Inventors: Gary T. Dane, Webster; Michael L. Latulippe, Derry; James B. Nordle, Hooksett, all of N.H.

[73] Assignee: Poly Vac, Incorporated, Manchester, N.H.

[*] Notice: This patent issued on a continued prosecution application filed under 37 CFR 1.53(d), and is subject to the twenty year patent term provisions of 35 U.S.C. 154(a)(2).

[21] Appl. No.: 794,413

[22] Filed: Feb. 5, 1997

Related U.S. Application Data

[63] Continuation of Ser. No. 600,474, Feb. 13, 1996, abandoned, which is a continuation of Ser. No. 375,897, Jan. 20, 1995, abandoned.

[51] Int. Cl.$^6$ ........................................................ A61L 9/00
[52] U.S. Cl. .......................... 422/300; 206/363; 206/370; 206/478; 206/483; 422/292; 422/297
[58] Field of Search .................................. 422/292, 297, 422/300; 206/363, 369, 370, 678, 480, 483, 564–565; 248/74.2, 68.1, 74.4

[56] References Cited

U.S. PATENT DOCUMENTS

| | | | |
|---|---|---|---|
| 4,135,868 | 1/1979 | Schainholz | 422/300 X |
| 4,229,420 | 10/1980 | Smith et al. | 422/310 |
| 4,643,303 | 2/1987 | Arp et al. | 422/300 X |
| 4,728,504 | 3/1988 | Nichols | 422/297 |
| 4,783,321 | 11/1988 | Spence | 422/300 |
| 4,798,292 | 1/1989 | Hauze | 206/439 |
| 4,854,475 | 8/1989 | Rihimaki et al. | 220/337 |
| 4,881,705 | 11/1989 | Kraus | 248/74.2 |
| 5,098,676 | 3/1992 | Brooks, Jr. | 422/292 |
| 5,284,632 | 2/1994 | Kudla et al. | 422/297 |
| 5,294,413 | 3/1994 | Riihimaki et al. | 422/297 |
| 5,384,103 | 1/1995 | Miller | 422/310 |
| 5,422,067 | 6/1995 | Barney | 422/300 X |

FOREIGN PATENT DOCUMENTS

| | | | |
|---|---|---|---|
| 3414679 | 10/1985 | Germany | B65D 85/00 |
| 2165218 | 4/1986 | United Kingdom | B65D 25/10 |

*Primary Examiner*—Krisanne Thornton
*Attorney, Agent, or Firm*—Hayes, Soloway, Hennessey, Grossman & Hage, P.C.

[57] ABSTRACT

A sterilization tray assembly for sterilizing, transporting and storing surgical instruments, having top and bottom mating enclosures. The mating enclosures each have a plurality of ports for permitting ingress and egress of gaseous sterilant. Resiliently deformable members are fitted in the top and bottom enclosures for clamping surgical instruments therebetween.

7 Claims, 5 Drawing Sheets

STERILIZATION AND STORAGE CONTAINER TRAY

This is a continuation of application Ser. No. 08/600,474 filed on Feb. 13, 1996 now abandoned, which is a continuation of application Ser. No. 08/375,897 filed on Jan. 20, 1995 now abandoned.

FIELD OF THE INVENTION

This invention relates to sterile container systems generally, and more particularly to container systems for the sterilization and subsequent sterile storage of medical surgical instruments and the like.

BACKGROUND OF THE INVENTION

Sterilization of reusable and delicate, precision surgical instruments and their subsequent sterile storage is of paramount concern to surgeons and hospitals. Sterilized surgical instruments are essential during surgical procedures to minimize the risk of infection.

Some example prior art patents which provide for sterilization and storage containers are Arp et al, U.S. Pat. No. 4,643,303; Nichols, U.S. Pat. No. 4,728,504, and Spence, U.S. Pat. No. 4,783,321. These prior art patents generally teach the use of baskets or trays designed to hold the instruments to be sterilized, and having apertures in the baskets which allow for gross drainage of condensation from the baskets first to the container floor below the basket, and from the container floor to the outside.

U.S. Pat. No. 4,643,303 describes a sterilization container enclosing an instrument basket within a box-like base and cover. The container also includes clamps mounted to the container by hinges for releasably holding the cover to the base. U.S. Pat. No. 4,783,321 describes a sterilization container enclosing an instrument basket within a base and cover. The container also includes a latch mechanism for releasably holding the cover to the base.

Most of the prior art, for example, Nichols U.S. Pat. No. 4,728,504, provide for the placement of the instruments on a removable basket or tray which includes apertures formed on the bottom of the tray to allow for the drainage of condensation. The domed configuration of the tray bottom in U.S. Pat. No. 4,728,504 reportedly allows for sufficient surface area contact with the instruments such that condensate may be held between the instruments and the tray after sterilization. Such a risk of airborne bacterial contamination of remaining condensation after sterilization increases during increased storage of the sterilized instruments. Thus, it is imperative to remove as much condensation as possible from the container and from the instruments after sterilization.

Hauze, U.S. Pat. No. 4,798,292, describes a non-locking sterilization container with apertures arranged in rows and columns enclosing a flat surfaced insert with apertures arranged in rows and columns such that the apertures in the container and the insert are vertically aligned. Pegs are inserted in the insert apertures to provide horizontal separation of the instruments during sterilization and subsequent presentation of the instruments. The flat surface of the insert and the pegs increase the risk of condensation remaining in proximity to the instruments after sterilization.

The foregoing discussion of the prior art was taken largely from Brooks, U.S. Pat. No. 5,098,676 which describes an improved sterilization tray assembly for sterilizing, transporting and storing instruments, which overcomes the aforesaid and other disadvantages of the prior art. Brooks provides a sterilization tray assembly comprising an upper tray section including a plurality of upper tray ports spaced in a predetermined pattern; a lower tray section including a plurality of lower tray ports spaced in a predetermined pattern; and locking means for engaging the upper tray section and the lower tray section to form a sealing contact between the upper and lower tray sections. A mat made of silicone rubber and sized to fit the tray is positioned between the tray sections. The mat has an upper surface and a lower surface, and includes a plurality of ports in the mat spaced in a predetermined pattern wherein the mat ports and the lower tray ports are in vertical alignment. The mat also has a plurality of upwardly tapered, vertical projections spaced in a predetermined pattern on the upper surface, the vertical projections having tips at their free ends to provide support for instruments above the upper surface; and a plurality of downwardly projecting support feet depending from the lower surface spaced in a predetermined pattern for spacing the lower surface above the lower tray section.

The sterilization tray assembly as described in Brooks U.S. Pat. No. 5,098,676 is available commercially from PolyVac, Inc. of Manchester, N.H., and has achieved substantial commercial success. However, while the silicone rubber mat as described in U.S. Pat. No. 5,098,676 provides a convenient support for many types of surgical instruments, certain instruments may shift when the tray assembly is being handled, and may possibly be damaged. The problem of shifting is particularly acute in the case of larger, heavier instruments such as laparoscopy instruments and endoscopes. Accordingly, PolyVac, Inc. and others such as Arp et al, U.S. Pat. No. 4,643,303 and Hauze, U.S. Pat. No. 4,798,292, have introduced sterilization trays including one or more instrument holding strips or pins designed to releasably hold selected surgical instruments in position in the tray assembly.

The present invention is an improvement over the sterilization, transporting and storage container trays such as described in U.S. Pat. Nos. 4,643,303, 4,798,292 and 5,098,676.

SUMMARY OF THE INVENTION

In one aspect, the present invention provides a sterilization, transporting and storage container tray assembly for a surgical instrument. The tray assembly includes top and bottom locking trays. The bottom tray includes a plurality of resiliently deformable support strips which position the instrument in the tray, and space the instrument from the inside bottom wall of the tray, leaving enough space underneath so that the instrument readily may be gripped and removed in the operating room. A plurality of resiliently deformable strips are affixed to the inside of the top so that the top and bottom trays are assembled and locked together, the instruments therein are held in position in the tray by the top and bottom resiliently deformable strips.

Ports are provided in the top and bottom trays for permitting ingress and egress of steam or other gaseous sterilants, and to facilitate condensation drainage.

Completing the sterilization, transporting and storage tray assembly are at least one pair of locking hinges or clips for locking the top and bottom trays together. The locking hinges or clips may comprise spring metal clips for example, as shown in FIG. 8 of the aforesaid U.S. Pat. No. 5,098,676 to Brooks.

BRIEF DESCRIPTION OF THE DRAWINGS

The foregoing and other objects of the present invention and various features and details of the operation and construction thereof are hereinafter more fully set forth with reference to the accompanying drawings, wherein like numerals depict like parts, and wherein.

DETAILED DESCRIPTION OF THE PREFERRED EMBODIMENT

Figure 1:
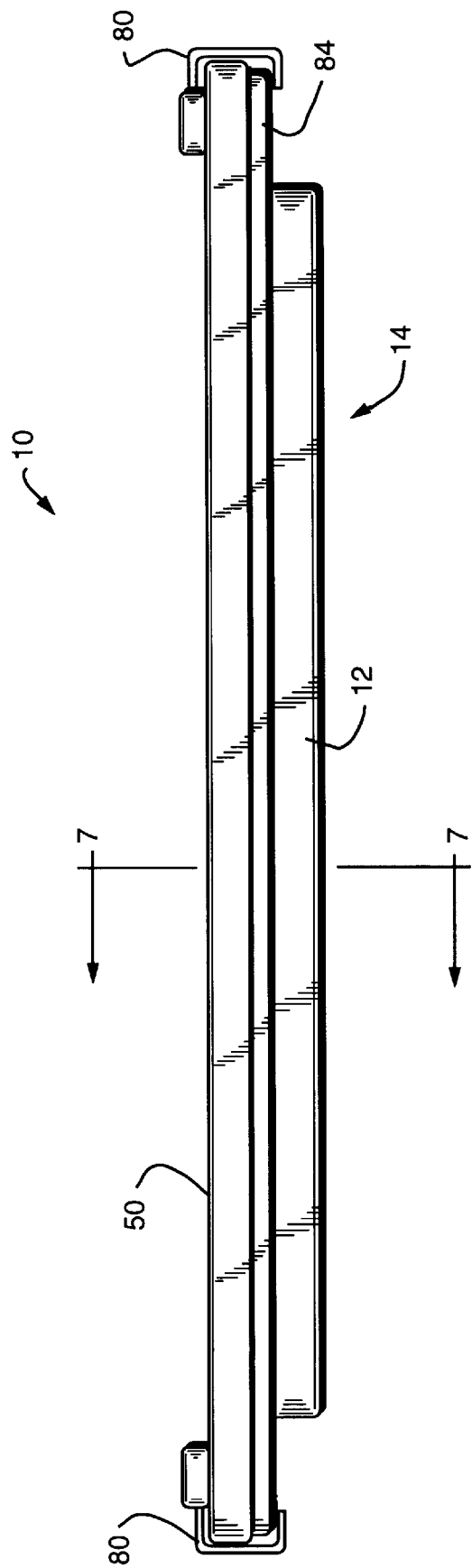
FIG. 1 is a side elevational view of the preferred embodiment of the invention showing the tray assembly in the closed and locked position.
Figure 2:
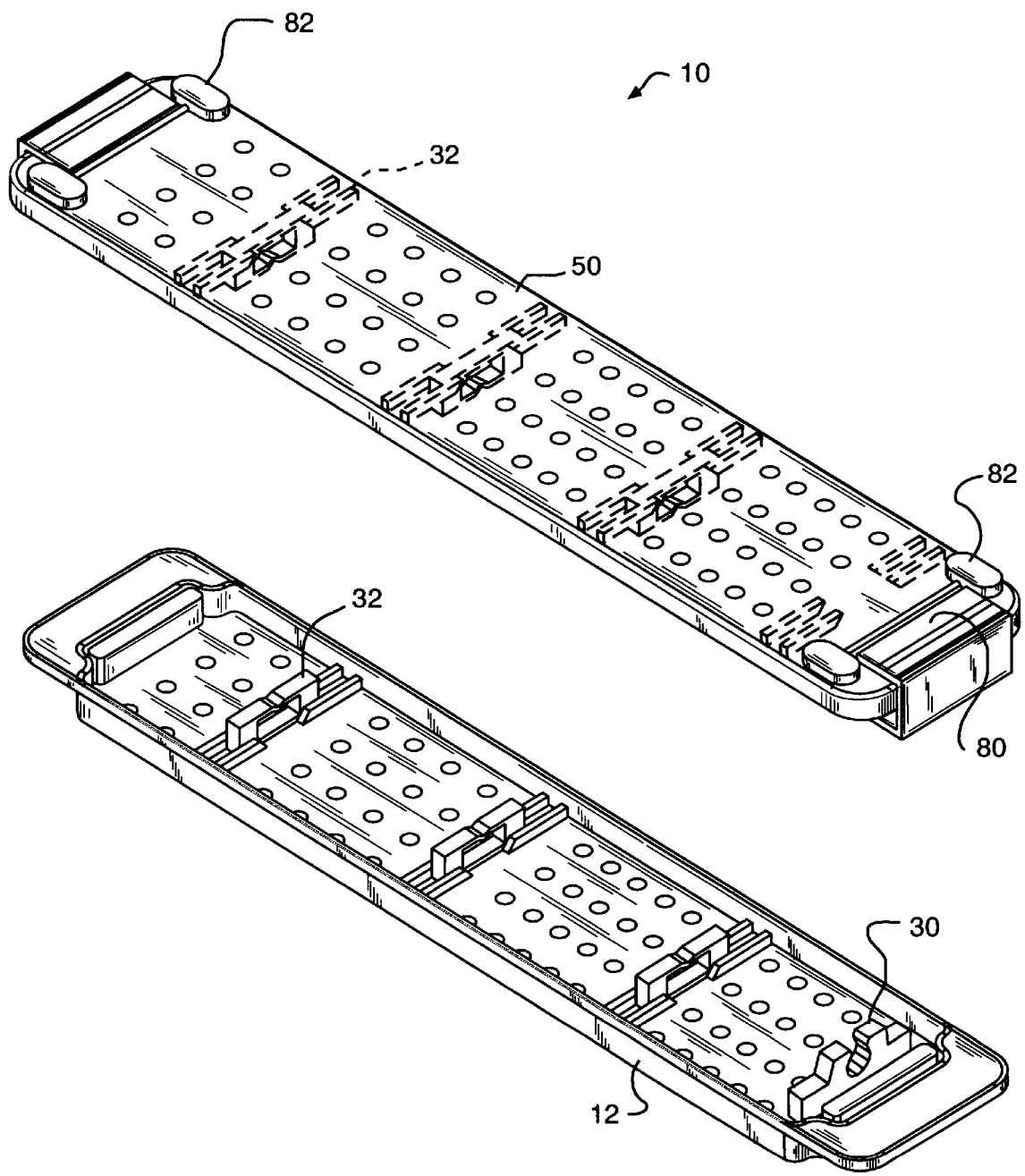
FIG. 2 is a partially exploded view of FIG. 1.
Figure 3:
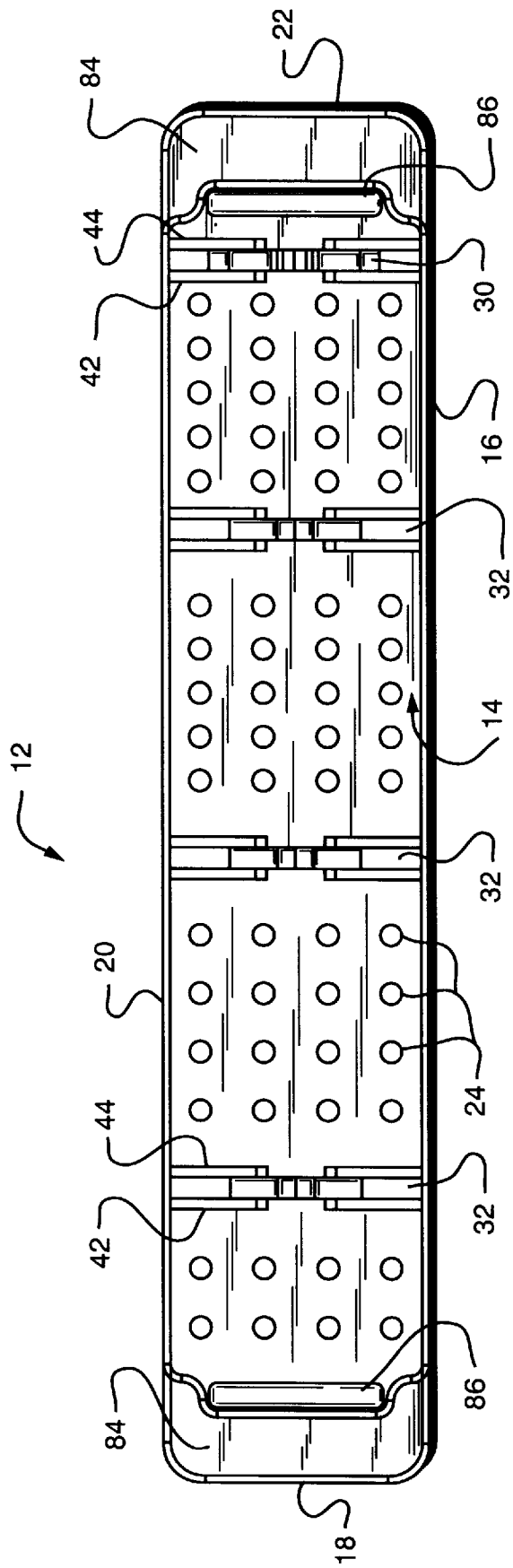
FIG. 3 is an overhead plan view of the tray assembly of FIG. 1, with the top tray removed.

Referring now to the drawings, and in particular to FIGS. 1–3, the sterilization, transporting and storage tray assembly of the present invention is indicated generally by numeral 10. The tray assembly 10 consists of an elongate, box-like bottom tray 12 having a bottom 14 and four generally perpendicular upwardly projecting continuous sidewalls comprising a front sidewall 16, a left sidewall 18, a back sidewall 20 and a right sidewall 22. Tray bottom 14 includes a plurality of spaced apertures 24 arranged in a predetermined pattern. Apertures 24 permit ingress and egress of steam or other gaseous sterilants, and allow for condensation drainage.

Figure 4:
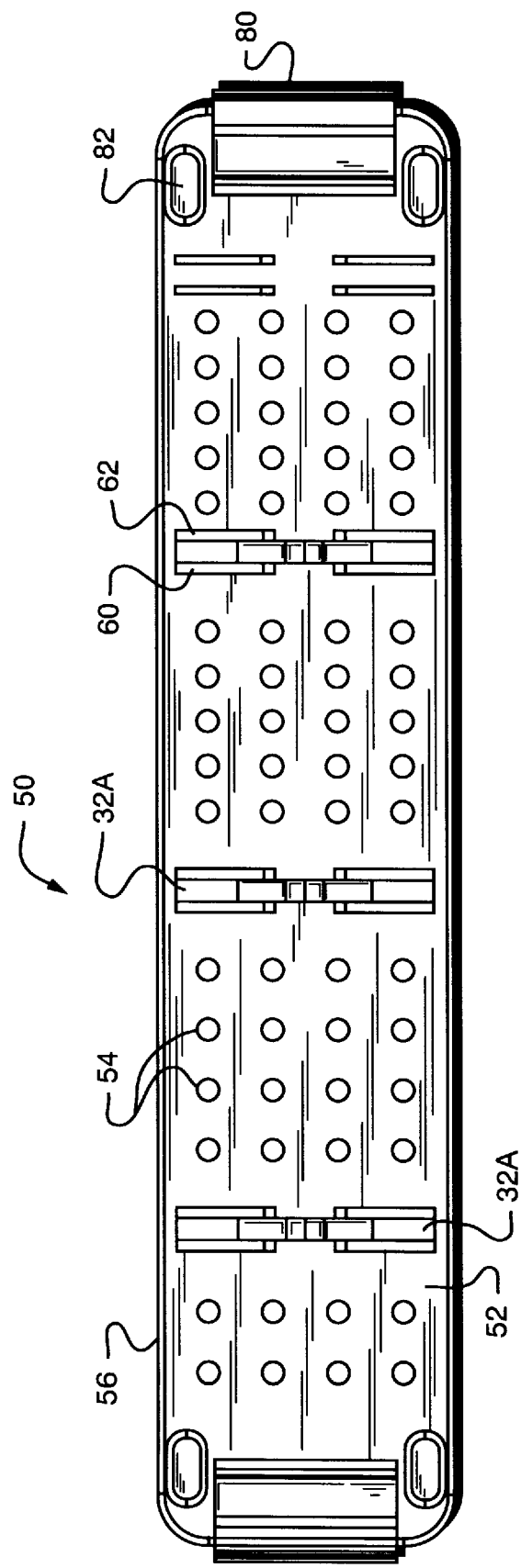
FIG. 4 is a view similar to FIG. 3, but taken from the inside of the top tray.

Referring also to FIG. 4, the tray assembly of the present invention also includes a top tray member 50 of an elongate box-like shape and includes a top surface 52 having a plurality of spaced apertures 54 arranged around the periphery of the top surface 52 to permit the ingress and egress of steam or other gaseous sterilants during sterilization, and drainage of condensation from the top surface 52. Top 50 includes a downwardly projecting lip section 56 which overlaps and engages the top portions of walls 16, 18, 20 and 22 of base 12 when the top 50 is locked upon the base 12. This sealing contact causes the steam of other gaseous sterilants to ingress and egress the container tray 10 only through apertures 24 and 54.

A feature and advantage of the present invention is to provide a surgical instrument delivery system which provides a high degree of protection for the storage, transport and sterilization of costly medical devices such as endoscopes and laparoscopy instruments. Accordingly, the present invention also provides means for releasably securing such instruments until they are needed during the course of a surgical procedure.

Figure 5:
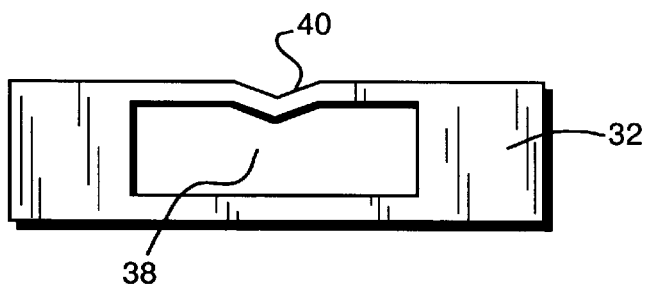
FIG. 5 is side elevational view showing details of one form of resiliently deformable holding strip employed in the tray assembly of the present invention.
Figure 6:
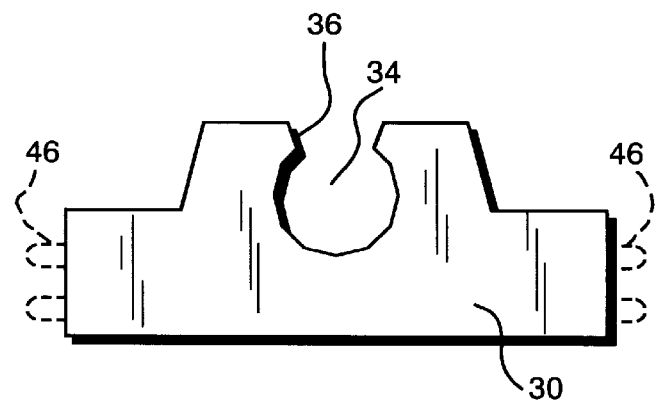
FIG. 6 is a view similar to FIG. 5, and showing another form of resiliently deformable holding strip employed in the tray assembly of the present invention.

Referring also to FIGS. 5–6, the surgical instrument delivery system made in accordance with the present invention comprises two or more resiliently deformable nesting strips 30, 32, affixedly positioned in the bottom tray 12 for supporting the medical instrument spaced from tray bottom 14. Strip members 30 and 32 typically are formed of a resiliently flexible, heat and moisture resistant material such as silicon rubber. Strip 30 includes a semi-circular opening 34 which is sized to releasably secure one end, typically the eye-piece of an endoscope or the like. Preferably, but not necessarily, the walls defining opening 34 comprise short segmented lengths or cords 36.

Strip 32 typically comprises an elongate silicon strip having a hollow 38. A recess 40 is formed along the top surface of strip 32 for receiving, supporting and locating the body of the medical instrument in the bottom tray 12.

Strips 30 and 32 are affixedly positioned in spaced relation in bottom tray 12. As seen in FIG. 3, strips 30 and 32 are friction fitted between pairs of rails 42, 44, which rails are integrally molded with the bottom tray 12. Alternatively, strips 30 and 32 may be affixedly positioned in bottom tray 12 by means of integrally formed tabs shown in phantom at 46 which are press fitted into cooperating apertures (not shown) formed in the side walls 16, 20 of tray bottom 12.

Figure 7:
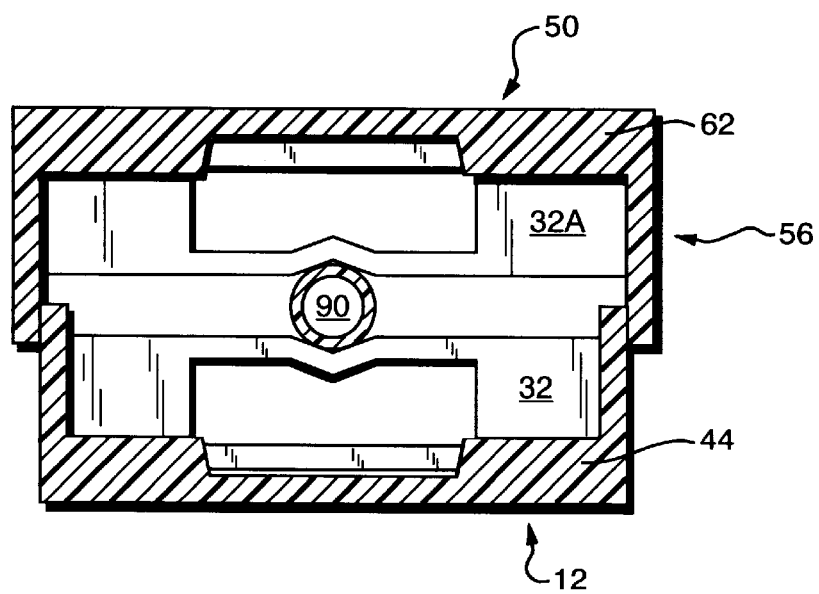
FIG. 7 is a cross-sectional view, taken along line 7—7 of FIG. 1.

Referring in particular to FIG. 4, a plurality of resiliently deformable strips 32A, similar to strips 32 are affixedly positioned in top 50, for example, by friction fit between integral rails 60, 62. Preferably, but not necessarily, strips 32 in top 50 overlie strips 32A in bottom 12 when the top and bottom are locked together. As can be seen in FIGS. 2 and 7, strips 32A are dimensional so that when the top 50 is locked to bottom 12, strips 32 and 32A are compressed against and clamp a surgical instrument 90 placed therebetween. Of course, strips 32A in the top 50 may be offset from strips 32 in the bottom 12 and still achieve this desired resilient clamping effect. Generally, however, it is not necessary to include a resiliently deformable strip in the top 50 overlaying strip 30.

Completing the sterilization and storage container tray of the present invention are C-shaped locking hinges 80 made of a flexible metal or plastic which are attached to top 50 by hinge pins (not shown) at bosses 82 which are integrally formed at the opposite ends of top 50 as shown in FIGS. 1 and 2. Locking hinges 80 pivot about hinge pins (not shown) between a locked position in which they engage a shoulder 84 integrally formed in the bottom tray 12, and non-locking position, as described in U.S. Pat. No. 5,098,676 to Brooks.

While particular embodiments of the present invention have been illustrated and described herein, it is not intended to limit the invention, and changes and modifications may be made thereon within the scope of the following claims. For example, a resiliently deformable pad 86 may be included adjacent at least one of the end walls of bottom 12 for cushioning the end(s) of an instrument mounted therein. Also varying numbers of various sized and nesting strips 32 may be employed, depending on the size and shape of the particular surgical instrument being carried. And, strips 32 may be located at various positions in the top and bottom trays.

Still other changes may be made without departing from the scope of the invention.

What is claimed is:

1. A sterilization tray assembly enclosure for sterilizing, transporting and storing delicate elongated surgical instruments which must be protected from shock, said instruments having a thickness falling within a predetermined range of thicknesses, the assembly including elongated top and bottom mating enclosures defining an interior space therebetween which can constitute a sterile space for holding a sterilized elongated surgical instrument after sterilization, said mating enclosures each including a plurality of ports for permitting the ingress and egress of gases for sterilant admitted to said interior space, means for locking said mating enclosures to one another and cooperating deformable members fitting in the top and bottom enclosures, respectively, for supporting and clamping said elongated delicate surgical instrument therebetween when said instrument is carried within the assembly, a plurality of said deformable members spaced along the long dimension of the container on opposite sides of a plane parallel to the top and bottom enclosures, said deformable members being positioned transversally of the long dimension of the enclosure, each said deformable member comprising a unitary construction consisting of a base strip, two side strips and a top strip which together define a hollow space therebetween, said base strips being adjacent one of said enclosures and said top strip being supported by said side strips within the interior space defined by said enclosure and spanning said space in position parallel to the other deformable members and closer to said plane than the thickness range of thicknesses of the surgical instrument, each of said top strips including a locating recess, and being sufficiently flexible to deflect and support said delicate surgical instrument along its length within said sterile space, and a resiliently deformable nesting having a semi-circular opening, positioned transversally of the long dimension of said enclosure adjacent one end of said bottom enclosure, for locating and releasably securing and cushioning one end of said instrument, said semi-circular opening being defined by a plurality of linear wall segments.

2. A tray assembly according to claim 1, wherein said resiliently deformable members in the top and bottom enclosures oppose one another when the top and bottom enclosures are mated to one another.

3. A tray assembly according to claim 1, wherein the resiliently deformable members in the top and bottom enclosures are offset relative to one another when the top and bottom enclosures are mated to one another.

4. A tray assembly according to claim 1, wherein the top enclosure has fewer resiliently deformable members than the bottom enclosure.

5. A tray assembly according to claim 1, wherein the resiliently deformable members are friction fit mounted to the top and bottom enclosures.

6. A tray assembly according to claim 5, wherein the top and bottom enclosures include pairs of integral rail members for holding said resiliently deformable members in position in said enclosures.

7. A tray assembly according to claim 11, wherein said resiliently deformable members comprise integral tabs for mating with apertures in the enclosures for holding said resiliently deformable members in position in said enclosures.

\* \* \* \* \*

UNITED STATES PATENT AND TRADEMARK OFFICE
CERTIFICATE OF CORRECTION

PATENT NO.   : 5,843,387
DATED        : December 1, 1998
INVENTOR(S)  : Dane et al It is certified that error appears in the above-identified patent and that said Letters Patent is hereby corrected as shown below:

Claim 7, Col. 6, line 19, "11" should be - -1- -.

Signed and Sealed this

Ninth Day of November, 1999

Attest:

Q. TODD DICKINSON

*Attesting Officer*    Acting Commissioner of Patents and Trademarks